United States Patent [19]

Willard

[11] 4,293,496
[45] Oct. 6, 1981

[54] 6(R)-[2-(8-HYDROXY-2,6-DIMETHYL-POLYHYDRONAPHTHYL-1)-ETHYL]-4(R)-HYDROXY-3,4,5,6-TETRAHYDRO-2H-PYRAN-2-ONES

[75] Inventor: Alvin K. Willard, Lansdale, Pa.
[73] Assignee: Merck & Co., Inc., Rahway, N.J.
[21] Appl. No.: 175,232
[22] Filed: Aug. 5, 1980

Related U.S. Application Data

[63] Continuation-in-part of Ser. No. 118,049, Feb. 4, 1980, abandoned.

[51] Int. Cl.$^3$ .................... C07D 309/30; C07C 59/11
[52] U.S. Cl. .............................. 260/343.5; 562/501; 424/279; 424/317
[58] Field of Search ................ 260/343.5; 562/501

[56] References Cited
U.S. PATENT DOCUMENTS

| | | | |
|---|---|---|---|
| 3,983,140 | 9/1976 | Endo et al. | 260/343.5 |
| 4,049,495 | 9/1977 | Endo et al. | 195/36 R |
| 4,137,322 | 1/1979 | Endo et al. | 424/273 R |
| 4,231,938 | 11/1980 | Monaghan et al. | 260/343.5 |
| 4,255,444 | 3/1981 | Willard | 260/343.5 |

OTHER PUBLICATIONS

Singer et al., Proc. Soc. Exper. Biol. Med., 102, 370 (1959).
Hulcher, Arch. Biochem, Biophys. 146, 422 )1971).
Brown et al., J. Chem. Soc., Perkin I, 1165 (1976).
Endo et al., J. Antibiotics XXXII, 852 (1979).
Derwent 15706c/09.

*Primary Examiner*—Ethel G. Love
*Attorney, Agent, or Firm*—William H. Nicholson; Mario A. Monaco

[57] ABSTRACT

The title compounds are prepared by saponifying the corresponding 8-acyloxy compounds, with strong base at elevated temperatures to remove the hindered acyl group without disrupting the rest of the molecule. The products are useful as intermediates in the synthesis of antihypercholesterolemia agents.

6 Claims, No Drawings

6(R)-[2-(8-HYDROXY-2,6-DIMETHYLPOLYHYDRONAPHTHYL-1)-ETHYL]-4(R)-HYDROXY-3,4,5,6-TETRAHYDRO-2H-PYRAN-2-ONES

This is a continuation-in-part of copending application, Ser. No. 118,049, filed Feb. 4, 1980, now abandoned.

SUMMARY OF THE INVENTION

This invention relates to a group of 6(R)-[2-(8-hydroxy-2,6-dimethylpolyhydronaphthyl-1)-ethyl]-4(R) hydroxy-3,4,5,6-tetrahydro-2H-pyran-2-ones and to the hydroxy acid form of said pyranones.

More specifically, this invention relates to a compound of the structure

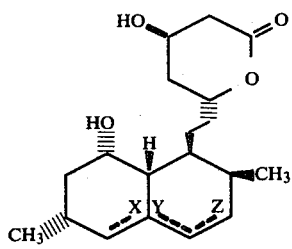

in which the dotted lines X, Y and Z represent possible double bonds, said double bonds being, when any are present, either X and Z together in combination or X, Y or Z alone, together with the free hydroxy acids of formula II, formed by opening the lactone ring.

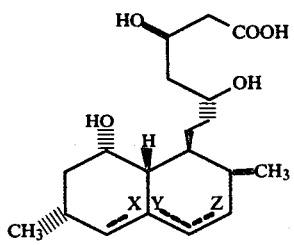

II

BACKGROUND OF THE INVENTION

It is known that certain mevalonate derivatives inhibit the biosynthesis of cholesterol, cf F. M. Singer et al, *Proc. Soc. Exper. Biol. Med.*, 102, 270 (1959) and F. H. Hulcher, *Arch. Biochem. Biophys.*, 146, 422 (1971). Nevertheless, the activity of these known compounds has not always been found to be satisfactory, i.e. to have practical application.

Recently, Endo et al, reported (U.S. Pat. No. 4,049,495, U.S. Pat. No. 4,137,322 and U.S. Pat. No. 3,983,140) the production of fermentation products which were quite active in the inhibition of cholesterol biosynthesis. The most active member of this group of natural products, now called compactin, was reported by Brown et al, *J. Chem. Soc. Perkin I* 1165 (1976) to have a complex mevalonolactone structure.

More recently Monaghan et al (U.S. Pat. No. 4,231,938) reported an even more potent inhibitor, $III_a$ having the structure

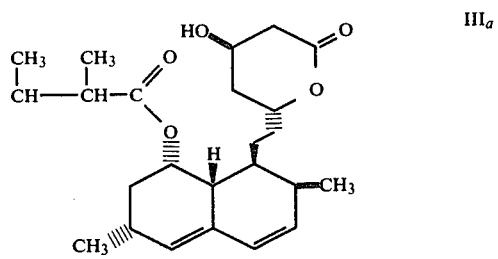

isolated from an entirely different fermentation. Albers-Schonberg et al (U.S. Ser. No. 154,157, filed May 28, 1980) described a dihydro $III_a$, designated $III_d$ in Flow Sheet B, of equal potency isolated from the same fermentation.

Patchett et al, (U.S. Ser. No. 118,050, filed Feb. 4, 1980, now abandoned) describe dihydro and tetrahydro derivatives of $III_a$ of different structures, prepared by the catalytic hydrogenation of $III_a$, designated $III_b$, $III_c$ and $III_e$ in Flow Sheet B.

The fermentation products reported by Endo included an α-methylbutyryl ester (ML236B) and the corresponding alcohol of the compactin ring system (ML236A). However, in the fermentation which produced $III_a$ and $III_d$, the only products isolated were the methylbutyryl esters, no free alcohol corresponding to these esters being detected.

The preparation of the starting material, $III_d$, as mentioned previously, is described by Albers-Schonberg et al in U.S. application, Ser. No. 154,157, filed May 28, 1980 and is a product of the following fermentation with a strain of *Aspergillus terreus*, ATCC No. 20542, designated MF-4845 in the culture collection of MERCK & CO., Inc. Rahway, N.J.

Preparation of Compound $III_d$

A. Fermentation

A tube of lyophilized culture MF-4845 was opened aseptically and the contents suspended in an unbaffled 250 ml Erlenmeyer flask (seed flask) containing approximately 10 ml of the Medium which has the following composition:

| Medium | |
|---|---|
| Corn steep liquor | 5 g |
| Tomato paste | 40 g |
| Oatmeal | 10 g |
| Glucose | 10 g |
| Trace Element Solution | 10 g |
| Distilled water | 1000 ml |
| pH 6.8 with NaOH | |

| Trace Element Solution: | |
|---|---|
| $FeSO_4 \cdot 7H_2O$ | 1000 mg |
| $MnSO_4 \cdot 4H_2O$ | 1000 mg |
| $CuCl_2 \cdot 2H_2O$ | 25 mg |
| $CaCl_2 \cdot 2H_2O$ | 100 mg |
| $H_3BO_3$ | 56 mg |
| $(NH_4)_6Mo_7O_{24} \cdot 4H_2O$ | 19 mg |
| $ZnSO_4 \cdot 7H_2O$ | 200 mg |
| Distilled Deionized Water | 1000 ml |

The inoculated flask was incubated for 24 hours at 28° C. on a 220 rpm shaker (2 inch throw). An unbaffled 2 liter Erlenmeyer flask containing 500 ml of the medium was then inoculated with 10 ml of the first stage fermentation growth from the seed mixture. This too was shaken 24 hours at 28° C.

A 200 gallon stainless steel fermentation vat was then charged with 485 liters of a medium comprising:

| Cerelose | 4.5% wt/vol |
|---|---|
| Peptonized Milk | 2.5% wt/vol |
| Autolyzed yeast | 0.25% wt/vol |
| Polyglycol P2000 | 0.25% vol/vol | whose pH was adjusted to 7.0. This was sterilized 15 minutes at 121° C. One liter of the second stage above was then charged and the mixture was incubated at 85 rpm for 12 hours then 130 rpm for 84 hours at 28° C. with an air flow of 5 cfm for 12 hours then 10 cfm for 84 hours.

B. Isolation

1. Extraction

Two batches of one hundred gallons of whole broth were combined, acidified with stirring to pH4.1 by careful addition of 800 ml of concentrated hydrochloric acid, and extracted by addition of 75 gal of ethyl acetate and further stirring for two hours.

About 25 lbs of a silicaceous filter aid was then added and the total slurry was pumped through a 24-inch filter press. An additional 75 gal of ethyl acetate was used to wash the press cake and continue the extraction, by reversing the direction of pumping through the press four times. Then all of the wash solvent was discharged from the press and combined with the first filtrate. The two-phase filtrate was allowed to settle, and the water layer removed. The ethyl acetate layer was washed with 10 gal of deionized water, the phases were allowed to separate and the ethyl acetate extracts were concentrated under vacuum to a residue of about 10 gal.

2. Lactonization

Ethyl acetate extracts from an additional three hundred gal of broth were added to the above extract and the volume was reduced to about thirty gal by vacuum distillation. About fifty gal of toluene was added, and the batch was concentrated under vacuum to 32 gal; this step was repeated; then sufficient new toluene was added to bring the volume to 75 gal. Without vacuum, the batch was brought to reflux and maintained there for two hours, with a temperature over 106° C.

This solution was then concentrated under vacuum to a small volume, which was further concentrated to an oily residue in a large rotary evaporator under vacuum.

3. Chromatography on Silica Gel

The extract obtained above was flushed free of other solvents by addition of 2 gal of methylene chloride and reconcentration to an oil.

The oily residue was dissolved in about 5 gal of ethyl acetate-methylene chloride (30/70; v/v) mixture, and a slurry was made by addition of 2.8 kg of silica gel.

The slurry was loaded as a level layer on the top of a 12 in.×50 in. silica gel column packed in the same solvent mixture.

Elution was with ethyl acetate-methylene chloride (40/60; v/v) at 800 ml/min. A forerun of 10 gal, then further fractions of 4 gal each were collected.

Fractions 6–10 inclusive were concentrated under vacuum to an oily residue which was dissolved in hot ethyl acetate, treated with decolorizing carbon, filtered hot, and cooled. Crystals of Compound $III_a$ were filtered off and the mother liquors were concentrated to an oil for further chromatography.

4. Rechromatography on Silica Gel

Mother liquor residues from similar broth extract work-ups equivalent to an additional 600 gal of fermentation production were combined with the above in methylene chloride solution. One-half of this solution was taken for further silica gel chromatography. A small aliquot showed a total solids content of 325 g. The solution was treated with 40 g of decolorizing carbon, filtered, and the cake rinsed with methylene chloride. The combined filtrate and washings were concentrated under vacuum to an oily residue. This was redissolved in 800 ml of ethyl acetate/methylene chloride (30/70; v/v) and slurried with 225 g of silica gel. The slurry was loaded on top of a 14×36 cm column bed of silica gel packed in the same solvent mixture. Development was with ethyl acetate/methylene chloride (40/60; v/v). A forecut of three liters was set aside; then fractions of 800 ml each were collected.

5. Chromatography on Reverse-phase Packing

Forty ml from fraction 12 of the above chromatography were concentrated to an oil weighing 500 mg and the oil redissolved in 5 ml acetonitrile. This acetonitrile solution was charged to a ⅜" OD by 6 ft long stainless steel chromatography column packed with preparative reverse-phase liquid chromatography column packing material "Bondapak C18/PorasilB" (Waters Associates, Inc., Mildford, Mass. 01757). The column was eluted with a mixture consisting of (v/v) 55% acetonitrile and 45% 0.05 M ammonium phosphate pH3. The elution volume between 1360 ml and 1700 ml was combined on the basis of refractive index detection. The organic solvent was removed in vacuo and the residual aqueous solution extracted with ethyl acetate. In vacuo removal of the ethyl acetate left 120 mg of compound which crystallized from a concentrated acetonitrile solution yielding crystals of Compound $III_d$, m.p. 129°–131° C.

Starting materials $III_b$, $III_c$ and $III_e$ as mentioned above are described in U.S. application, Ser. Nos. 118,050, filed Feb. 4, 1980 by Patchett et al., now abandoned, in accordance with the following Flow Sheet and preparative methods extracted therefrom.

FLOW SHEET A

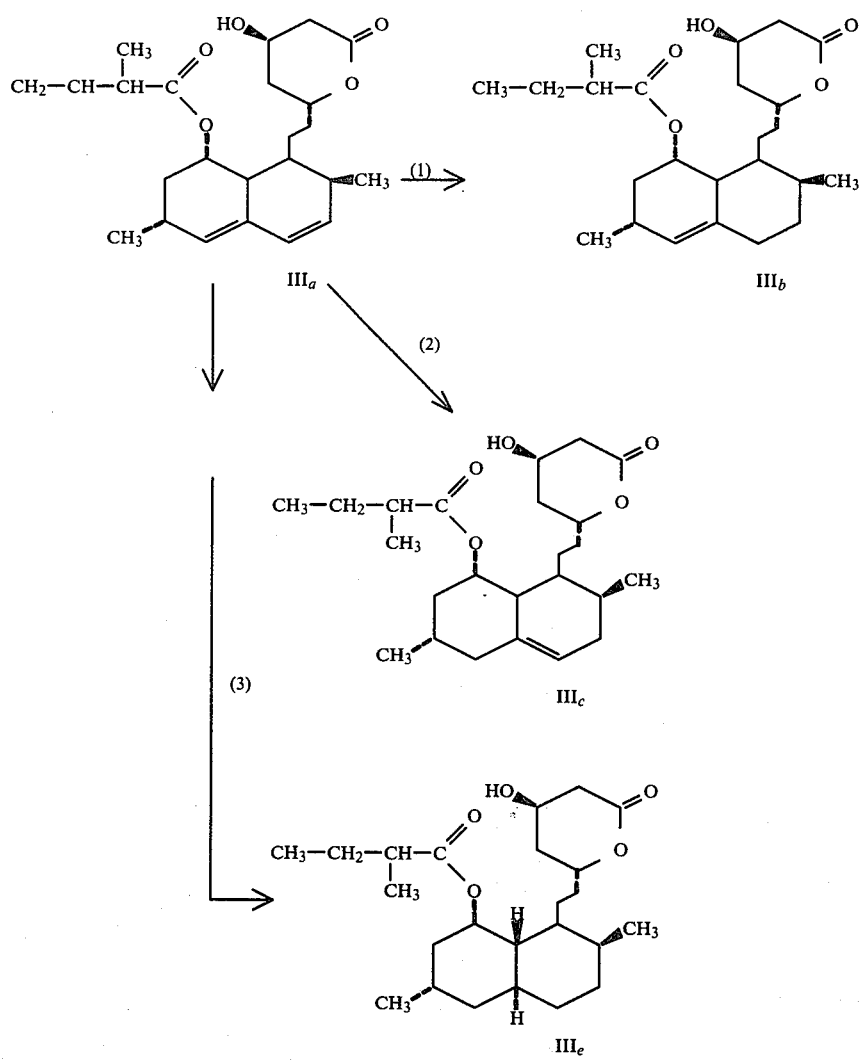

Reactions and Reagents (1) Hydrogenation at room temperature and one atmosphere over tris-(triphenylphosphine)chlororhodium in toluene.
(2) Hydrogenation at room temperature and one atmosphere over 5% palladium on calcium carbonate, in ethanol.
(3) Hydrogenation at room temperature and one atmosphere over platinum oxide in ethyl acetate.

Preparation of 6α[2-(8β-2-S-methylbutyryloxy-2β, 6α-dimethyl-1,2,3,4,6,7,8,8a-octahydronaphthyl-1)ethyl]-4β-hydroxy-3,4,5,6-tetrahydro-2H-pyran-2-one, III$_b$ A mixture of 50 mg (0.1236 mmol) of Compound III$_a$ and an equal molar amount (114.35 mg, 0.1236 mmol) of tris-(triphenylphosphine)chlororhodium in 10 ml of dry toluene was hydrogenated at room temperature for 6 days, with a total uptake of 14.6 ml of hydrogen. The mixture was evaporated in vacuo to dryness. The red residue was subjected to preparative thin-layer chromatography on silver nitrate impregnated silica plates and was developed twice in 10% ethyl acetate-ether system. The yield of compound III$_b$ was 22.3 mg.

Mass spectrum (M/$e$)
    406 (m+)
    304 (m-102)
    286 (m-102-18)
nmr (CDCl$_3$, 300 MHz)
    δ4.37 (m,1H)
    4.60 (m,1H)
    5.34 (d of t, J=2.5 Hz, 1H)
    5.41 (m,1H)

Preparation of 6α[2-(8β-2-(S)-methylbutyryloxy-2β,6α-dimethyl-1,2,3,5,6,7,8,8a-octahydronaphthyl-1)ethyl]-4β-hydroxy-3,4,5,6-tetrahydro-2H-pyran-2-one, III$_c$ A solution of 80.91 mg (0.2 mmol) of Compound III$_a$ in 10 ml of absolute ethanol, in the presence of an equal weight of 5% Pd on CaCO$_3$ was hydrogenated at 1 atmosphere until an uptake of one mole equivalent of hydrogen was observed. The catalyst was then removed by filtration and the filtrate was evaporated to dryness (81 mg). After a purification by preparative thinlayer chromatography to remove a small amount of by-product tetrahydro compound, 72 mg of the 1,4 reduction product III$_c$ was isolated.

Mass Spectrum (M/$\underline{e}$)
 406 (m+)
 304 (m-102)
 286 (304-H2O)
nmr (CDCl$_3$, 300 MHz)
 δ4.38 (m, 1H
 4.64 (m, 1H)
 5.28 (d of t, J=3.5 Hz, 1H)
 5.48 (m, 1H)

Preparation of 6α-[2-(8β-2(S)-methylbutyryloxy-2α,6β-dimethyl-1,2,3,4,4aα,5,6,7,9,8a-decahydronaphthyl-1)-ethyl]-4β-hydroxy-3,4,5,6-tetrahydro-2H-pyran-2-one, III$_e$ A solution of 80.91 mg (0.2 mmol) of Compound III$_a$ in 10 ml of ethyl acetate was hydrogenated in the presence of an equal weight of platinum oxide at one atmosphere. An exact 2 mole equivalent of hydrogen was consumed within 1 hour. The catalyst was removed by filtration and the filtrate was concentrated to dryness to give an oil. The cis and trans isomers were separated by preparative thin-layer chromatography on silica gel plates (10% ethyl acetate-ether system, bands detected by water spray). The trans isomer III$_e$ appears as the more polar spot, compared to the cis isomer, and 60 mg was isolated.

Mass spectrum (M/$\underline{e}$)
 408 (m+)
 323 (m-85)
 306 (m-102)
nmr (CDCl$_3$, 300 MHz)
 δ 4.36 (broad singlet, 1H)
 4.59 (m,1H)
 5.19 (d of t, J=2.5 Hz, 1H)

DESCRIPTION OF THE INVENTION abandoned, which application is incorporated herein by reference.

The preparation of the novel alcohols of this invention is carried out as shown in Flow Sheet B by heating the esters III$_{a-e}$ with an alkali metal hydroxide such as lithium hydroxide, potassium hydroxide or sodium hydroxide in a protic solvent such as water or alcohols for extended periods. Preferred is lithium hydroxide in water at reflux for about 50-72 hours or under pressure at higher temperatures of 120°-180° C. for shorter times of 8-24 hours.

The pyranone ring readily opens but the removal of the side chain acyl group is not easily effected. The heating must be prolonged and/or pressure must be used. An inert atmosphere is also helpful. It is quite unexpected that molecules with so many highly sensitive functional centers can withstand the harsh conditions necessary for removal of the highly hindered α-methylbutyryl ester. It is especially unexpected to find the yields high.

The products are isolated by acidification and extraction with organic solvents which provides the hydroxy acid form II$_{a-e}$. These hydroxy acids can be relactonized by heating a solution of the acid in an appropriate organic solvent such as toluene or benzene in an apparatus permitting continuous separation of the water formed.

The alcohols which form this invention comprise Structures I$_{a-e}$ as well as the hydroxy acids II$_{a-e}$ in Flow Sheet B resulting from opening of the lactone rings.

Flow Sheet B shows the preparation of these compounds. The stereochemical relationships of the key portions of the molecules important in the d and e series, is shown in Table I. Each of the alcohols I$_{a-e}$ which are the subject of this invention contains seven or eight chiral centers. The relative and absolute configuration at each of these asymmetric carbon atoms is known and is depicted for formulae I$_{a-e}$ in Flow Sheet B and Table I.

FLOW SHEET B

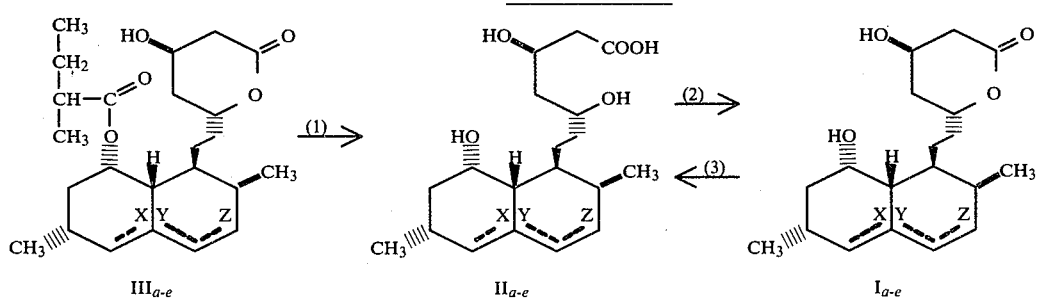

III$_{a-e}$  II$_{a-e}$  I$_{a-e}$

Reagents
(1) M$^+$OH$^-$ heated in protic solvent with or without pressure. M$^+$ is alkali metal followed by acidification.
(2) heating in toluene or benzene
(3) NaOH in aqueous ethanol at ambient temperature followed by careful acidification with dilute acid.

We have found that the α-methylbutyryl group in Compound III$_a$ and its hydro-derivatives, both natural and synthetic, can be removed cleanly to produce a family of 6(R)-[2-(8-hydroxy-2,6-dimethylpolyhydronaphthyl-1)-ethyl]-4(R)-hydroxy-3,4,5,6-tetrahydro-2H-pyran-2-ones which are themselves hypocholesterolemic agents and which are extremely useful as intermediates for the preparation of novel esters which are even more potent in this use. Esters which are hypocholesterolemic agents are described in the application of Willard et al., U.S. Ser. No. 118,051, filed Feb. 4, 1980, now

TABLE I

Stereochemistry of Compounds in Flow Sheet A

| Series | Double Bonds Present | Structure |
|---|---|---|
| a | x and z | 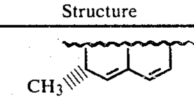 |
| b | x | 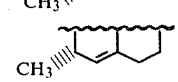 |
| c | y | 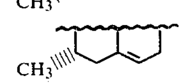 |

TABLE I-continued

Stereochemistry of Compounds in Flow Sheet A

| Series | Double Bonds Present | Structure |
|---|---|---|
| d | z | 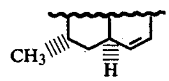 |
| e | none | 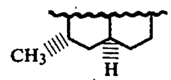 |

More specifically, for alcohol $I_a$ the Cahn, Ingold, Prelog designations for the absolute configurations are 4(R), 6(R), 1'(S), 2'(S), 6'(R), 8'(S) and 8a'(R). [R. S. Cahn, E. Ingold and V. Prelog, *Ang. Chem. Int. Ed.* 5, 385 (1966)].

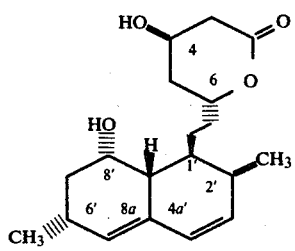

As indicated in the structural formulae $I_{a-e}$, all of these compounds have the same spatial orientation of groups at each chiral carbon atom and therefore belong to the same stereochemical series. The R-S designation for each center may not be identical to that found for alcohol $I_a$ because of the details of the sequence rules for determining that designation. In the two alcohols $I_d$ and $I_e$, which have an additional chiral carbon atoms not present in $I_a$, the hydrogen at carbon 4a' is in the down (or α) orientation as depicted, giving a trans ring junction.

These alcohols are themselves inhibitors of HMG-CoA reductase, but they are especially useful as intermediates for the synthesis of ester analogs of the above mentioned Compounds $III_{a-e}$. Thee synthetic analogs are more potent than the alcohols from which they are derived. For example, novel esters of the 8-hydroxy group are prepared, as described by Willard et al., U.S. Application, Ser. No. 118,051, filed Feb. 4, 1980, now abandoned by protecting the hydroxyl group on the pyranone and then acylating the 8-hydroxy, after which the protecting group is removed.

These syntheses are represented by the following Flow Sheet C, and described in the preparative descriptions thereafter.

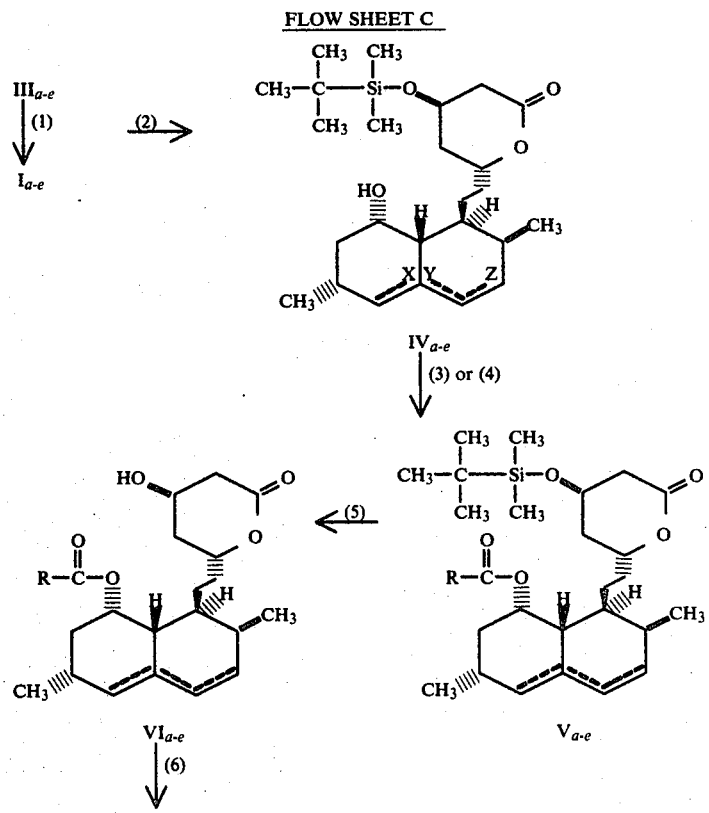

FLOW SHEET C

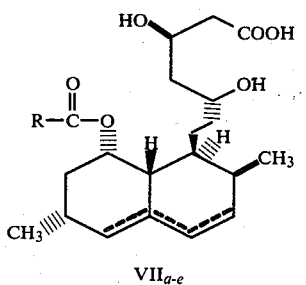

VII$_{a-e}$

Definitions—X,Y and Z and R as defined in specification and series a-e as defined in Table I.

Reactions
(1) Lithium hydroxide and heat followed by acidification.
(2) t-Butyldimethylchlorsilane and imidazole in DMF at ambient temperatures in an inert atmosphere.
(3) Treatment with RCOCl and 4-dimethylaminopyridine in pyridine solution preferably under inert atmosphere.
(4) Treatment with RCOOH and N,N'-dicyclohexylcarbodiimide and 4-pyrrolidinopyridine in dichloromethane, preferably under an inert atmosphere.
(5) Three equivalents of tetrabutylammonium fluoride and four equivalents of acetic acid per equivalent of ester in THF, preferably in an inert atmosphere.
(6) Aqueous alkali followed by careful acidification with dilute acid.

The 4-hydroxyl on the pyranone ring, of alcohols I$_{a-e}$ is first protected with a t-butyldimethylsilyl group by reaction with t-butyldimethylchlorosilane in an inert atmosphere at ambient temperatures in the presence of an acid acceptor such as imidazole to provide the protected alcohols IV$_{a-e}$. The 8'-hydroxyl on the polyhydronaphthyl ring is then acylated in one of two ways. The first comprises treatment with the acid chloride of the desired acyl group in pyridine in the presence of 4-dimethylaminopyridine as a catalyst. The second comprises treatment of the 8'-polyhydronaphthol with the free acid of the desired acyl group and an N,N'-dicyclohexylcarbodiimide with 4-pyrrolidinopyridine as a catalyst in dichloromethane. These procedures give the protected esters V$_{a-e}$. The removal of the silyl protecting group from the 4-hydroxyl of the pyranone ring is then carried out, using three equivalents of tetrabutylammonium fluoride and four equivalents of acetic acid per equivalent of esters V$_{a-e}$, to give the desired compounds VI$_{a-e}$. The ratio of reagents in this last reaction is critical to the yield of the process and the purity of the products.

The acyl groups thus put on the 8'-hydroxyl may be those in which R in VI$_{a-e}$ and VII$_{a-e}$ is:
C$_{1-8}$ straight chain alkyl,
C$_{3-10}$ branched chain alkyl except (S)-2-butyl,
C$_{3-10}$ cycloalkyl,
C$_{2-10}$ alkenyl,
C$_{1-10}$ CF$_3$ substituted alkyl,
halophenyl,
phenyl-C$_{1-3}$ alkyl,
substituted phenyl-C$_{1-3}$ alkyl in which the substituent is halo, such as chloro, bromo, or iodo, C$_{1-3}$ alkyl or C$_{1-3}$ alkoxy.

Especially to be preferred are:
C$_{2-5}$ straight chain alkyl,
C$_{3-10}$ branched chain alkyl except (S)-2-butyl,
C$_{3-10}$ cycloalkyl, or
C$_{3-10}$ alkenyl in which the unsaturation is not in conjugation with the carbonyl.

The salts of the free hydroxy acids (Compounds VII$_{a-e}$) are prepared by heating the lactones in aqueous base solutions, the cation of the base being the desired cation. Pharmaceutically acceptable salts include the alkali salts (sodium, potassium, lithium, etc.), the alkaline earth salts (calcium, strontium etc.), the ammonium salts and substituted ammoniums such as tetra(C$_{1-3}$ alkyl)ammonium (e.g. tetramethylammonium) and amine salts derived from common amines and amino acids.

Preparation of 6(R)-[2-(8'(S)-hydroxy-2(S)-dimethyl-1',2',6',7',8',8a'(R)-hexahydronaphthyl)ethyl]-4(R)-(dimethyl-tert-butylsilyloxy)-3,4,5,6-tetrahydro-2H-pyran-2-one, IV$_a$ A mixture of the alcohol I$_a$ (18.3 g, 57.1 mmol), 21.5 g (142.8 mmol) of tertbutyldimethylchlorosilane and 19.4 g (285.6 mmol) of imidazole in 200 ml of N,N-dimethylformamide was stirred at 20° under a nitrogen atmosphere for 18 hours. The reaction mixture was then diluted with 1500 ml of ether and washed successively with water, 2% aqueous hydrochloric acid, water and saturated sodium bicarbonate. The ether solution was dried over MgSO$_4$, filtered and reduced to a volume of 1 L. After addition of 600 ml of hexane, the volume was reduced to 600 ml on a steam bath. The product crystallized at room temperature which after isolation and air drying gave 13.7 g of a white cottony solid. The mother liquors were reduced to 250 ml and a second crop of crystals was isolated after standing at 0° overnight. The combined yield was 17.13 g (69%) of the title compound, VI$_a$, as a white cottony solid: mp 142°-144° (vac); NMR (CDCl$_3$) δ 0.10 (s,6,(CH$_3$)$_2$Si), 0.90 (s,9,(CH$_3$)$_3$CSi), 1.19 (d,3,J=7 Hz, CH$_3$), 2.58 (d,2,J=4 Hz, pyran C$_3$H's), 4.3 (m,2, pyran C$_4$H and naphthalene C$_8$H) 4.70 (m,1, pyran C$_6$H), 5.57 (m,1,naphthalene C$_5$H), 5.58 (dd,1, J=6,10 Hz, naphthalene C$_3$H), 6.03 (d,1,J=10 Hz, naphthalene C$_4$H).

Anal. Calcd. for C$_{25}$H$_{42}$O$_4$Si: C, 69.08, H, 9.74. Found: C, 69.46; H, 9.83.

Preparation of 6(R)-[2-(8'(S)-2'',2''-dimethylpropanoyloxy-2'(S),6'(R)-dimethyl-1',2',6',7',8',8a'(R)-hexahydronaphthyl-1'(S))ethyl]-4(R)-(dimethyl-tert-butylsilyloxy)-3,4,5,6-tetrahydro-2H-pyran-2-one, $V_a$ A solution of 6.0 g (13.8 mmol) of the alcohol $V_a$ and 200 mg of 4-dimethylaminopyridine in 50 ml of pyridine was cooled to 0° under a nitrogen atmosphere. To this stirred solution was added 6.8 ml (6.65 g, 55.2 mmol) of pivaloyl chloride over 15 minutes. The reaction mixture was stirred at 0° for 1 hour and then at 20° for 4 days. The reaction mixture was diluted with 750 ml of ether and washed with 2% aqueous hydrochloric acid until the wash was acidic and then with saturated $NaHCO_3$ solution. After drying over $MgSO_4$ the solution was filtered and evaporated to give 7.81 g of the title compound $V_a$ as a light orange oil: NMR ($CDCl_3$) δ 0.09 (s,6($CH_3$)$_2$Si), 0.88 (s,9,($CH_3$)$_3$CSi), 1.28 (s,9, ($CH_3$)$_3$C$CO_2$—), 2.57 (d,2,J=4 Hz, pyran $C_3$H's), 4.32 (m,1,pyran $C_4$H), 4.63 (m,1,pyran $C_6$H), 5.34 (m,1,naphthalene $C_8$H), 5.54 (m,1,naphthalene $C_5$H), 5.78 (dd,1,J=6, 10 Hz, naphthalene $C_3$H), 6.03 (d,1,J=10 Hz, naphthalene $C_4$H).

The following esters of structure $V_a$ are prepared according to the foregoing procedure using an equivalent quantity of the appropriate acid chloride:

$$R-\overset{O}{\underset{\|}{C}}-Cl$$

| $R-\overset{O}{\underset{\|}{C}}-O-$ | NMR($CDCl_3$,δ) |
|---|---|
| 4-F-C$_6$H$_4$-$CO_2$— | 7.10(t,2,J = 8Hz,p-FPh—) 8.03(dd,2,J = 5,8Hz,p-FPh—) |
| $CH_3CO_2$— | 2.02(s,3,$CH_3CO_2$—) |
| $CH_3\text{-}CH(CH_3)\text{-}C(=O)\text{-}O-$ | 1.19(d,J = 7Hz,α-$CH_3$ ester) 1.21(d,J = 7Hz,α-$CH_3$ ester) Total 3H |
| $(CH_3)_2CHCH_2CO_2$— | 0.83(d,6,J = 6Hz,$(CH_3)_2$CH—) |
| $(CH_3)_2CHCO_2$— | 1.13 (d,6,J = 6Hz$(CH_3)_2$CH) |
| $CH_3(CH_2)_3CO_2$— | 0.95 (t,3,J = 7Hz,$CH_3$—$(CH_2)_3$— |
| Adamantyl-$CO_2$— | 1.60–2.08 (m,15,Adamantyl) |
| $(CH_3CH_2)_3CCO_2$— | 0.87(m,9,$CH_3CH_2CH_2(CH_3CH_2)_2CCO_2$) |
| (t-Bu)-$CO_2$— | |
| cyclopentyl-$CO_2$— | |
| (H,CH$_3$ substituted)-$CO_2$— | |
| $CH_3(CH_2)_8CO_2$— | |
| $\text{(isopropenyl-C)}-CO_2-$ | 1.28(s,6,$(CH_3)_2CCO_2$) 2.20(s,3,$CH_3$—C=$CH_2$) 3.86(m,2,$CH_2$=C) |

Preparation of 6(R)-[2-(8'(S)-phenylacetoxy-2'(S),6'(R)-dimethyl-1',2',6',7',8',8a'(R)-hexahydronaphthyl-1'(S))-ethyl]-4(R)-(dimethyl-tert-butylsilyloxy)-3,4,5,6-tetrahydro-2H-pyran-2-one, $V_a$ A solution of 434 mg (1.0 mmol) of the alcohol $IV_a$ 204 mg (1.5 mmol) of phenylacetic acid, and 309 mg (1.5 mmol) of N,N'-dicyclohexylcarbodiimide in 10 ml of dichloromethane was treated with 22 mg (0.15 mmol) of 4-pyrrolidinopyridine and stirred at 20° under a nitrogen atmosphere. After 3 days the solvent was removed in vacuo and the residue was suspended in 25 ml of ether and filtered. Evaporation of the filtrate gave a viscous oil which was chromatographed on a 3×15 cm column of silica gel (230–400 mesh). Elution (under air pressure) with ether-hexane (1:1,v:v) gave 460 mg (83%) of the title compound as a viscous oil: NMR ($CDCl_3$) δ 0.10 (s,6,($CH_3$)$_2$Si), 0.90 (s,9,($CH_3$)$_3$CSi), 3.58 (s,2,Ph$CH_2$—) 5.34 (m,1, naphthalene $C_8$H), 7.30 (s,5,Ph).

The following esters of structure $V_a$ were prepared according to the proceding procedure using an equivalent quantity of the appropriate acid and dicyclohexylcarbodiimide.

| $R-\overset{O}{\underset{\|}{C}}-O-$ | NMR($CDCl_3$,δ) |
|---|---|
| cyclopropyl-$CO_2$— | 0.78–1.02(m,4,cyclopropane) |
| $CF_3\text{-}CH(CH_3)\text{-}CH_2CO_2-$ | 1.04 (d,3,J = 7Hz,$CH_3CHCF_3$) |
| $(CH_3)_2C=CH\text{-}CO_2-$ | 1.88(s,3,$CH_3$C=C) 2.17(d,3,J = 2Hz,$CH_3$C=C) 5.68 (brs,1,C=CH—) |
| $CH_2=C(CH_3)\text{-}CO_2-$ | 1.80 (s,3,$CH_3$C=C) 4.86,4.92(s,2,$CH_2$=C) |

Preparation of 6(R)-[2-(8'(S)-2,2-dimethylpropanoyloxy-2'(S),6'(R)-dimethyl-1',2',6',7',8',8a'(R)-hexahydronaphthyl-1'(S))ethyl]-4(R)-hydroxy-3,4,5,6-tetrahydro-2H-pyran-2-one, $VI_a$ To a solution of 10.0 g (31.7 mmol) of $Bu_4N^+F^-\cdot 3H_2O$ and 2.4 ml (2.5 g, 42.3 mmol) of acetic acid in 50 ml of tetrahydrofuran was added 7.81 g (13.8 mmol) of the silyl ether $VI_a$ in 50 ml tetrahydrofuran. This mixture was stirred at 20° under a nitrogen atmosphere for 18 hours. The reaction mixture was diluted with 700 ml of ether and washed successively with 2% aqueous hydrochloric acid, water and saturated aqueous $NaHCO_3$. The organic solution was dried ($MgSO_4$) and filtered. Evaporation of the solvent left 6.45 g of an off-white solid. This material was crystallized from 100 ml of butyl chloride and the isolated crystals were dried at 35°/0.01 mm Hg for four hours to give 4.0 g (72%) of the title compound as nearly white needles: mp 167.5°–170.5° (vac); NMR ($CDCl_3$) δ 0.88 (d,3,J=7 Hz,$CH_3$), 1.08 (d,3,J=7 Hz, $CH_3$),1.19 (s,9,($CH_3$)$_3$C), 2.67 (d,2,J=4 Hz, pyran $C_3$H's), 4.39 (m,1,pyran $C_4$H), 4.65 (m,1,pyran $C_6$H), 5.36 (m,1, naphthalene $C_8$H) 5.55 (m,1,naphthalene $C_5$H), 5.80 (dd,1,J=6,10 Hz, naphthalene $C_3H$), 6.04 (d,1,J=10 Hz, naphthalene $C_4H$); HPLC (4.6 mm.×25 cm Partisil 10 PAC, 10% isopropanol/hexane, 4 ml/min) retention time 4.4 min.

Anal. Calcd. for $C_{24}H_{36}O_5$: C,71.25; H, 8.97. Found: C,71.40; H, 8.93.

Esters $VI_a$ in the following table are prepared according to the procedure of the preceding Example, using an equivalent quantity of the appropriate silylether $V_a$.

| $RCO_2-$ | MP(°C.) |
|---|---|
| $CH_3$-C($CH_3$)($CO_2-$)-$CH_3$ | 139-148 |
| F-C$_6H_4$-CO$_2-$ | 119.5-120.5 (vac) |
| $(CH_3)_2CHCH_2CO_2-$ | 126-128 |
| $(CH_3)_2CHCO_2-$ | 144-147 |
| $CH_3(CH_2)_3CO_2-$ | |
| $CH_3CO_2-$ | 153-156* (vac) |
| cyclopropyl-$CO_2-$ | 116-119 |
| $CF_3CH(CH_3)CH_2CO_2-$ | 110-113 |
| benzyl-$CH_2CO_2-$ | 109-112 |
| norbornyl-$CO_2-$ | 155-158* |
| $CH_3$-cyclopropyl($CO_2-$)-$CH_3$ | 113-118 |
| $CH_2=C(CH_3)CO_2-$ | 116-119 |
| $(CH_3CH_2)_3CCO_2-$ | 129-132 |
| chiral-$CO_2-$ (H/$CH_3$) | 126-129 |
| cyclopentyl-$CO_2-$ | 81-83 |
| $(CH_3)_2$C(–)–$CO_2-$ | 75-78 |
| tert-C–$CO_2-$ | |

*contains 0.1 mol of butyl chloride as solvate
**contains 0.05 mol of cyclohexane as solvate Using procedures substantially as described in the foregoing experimental procedures there are prepared the corresponding 8'-acyloxy compounds in the $VI_{b-e}$ series.

The 8-acyloxy compounds prepared from the novel 8-alcohols of this invention are useful as antihypercholesteremic agents for the treatment of atherosclerosis, hyperlipemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but a daily dosage for adults is within a range of from about 2 mg to 2000 mg (preferably 10 to 100 mg) given in three or four divided doses. Higher doses may be favorably applied as required.

The compounds of this invention also have useful anti-fungal activities. For example, they may be used to control strains of Penicillium sp., *Aspergillus niger*, Cladosporium sp., *Cochliobolus miyabeanus* and *Helminthosporium cynodnotis*. For those utilities they are admixed with suitable formulating agents, powders, emulsifying agents or solvents such as aqueous ethanol and sprayed or dusted on the plants to be protected.

The preparations of the novel compounds of this invention are exemplified by the following examples.

EXAMPLE 1

Preparation of 6(R)-[2-(8'(S)-Hydroxy-2'(S),6'(R)-dimethyl-1',2',6',7',8',8'a(R)-hexahydronaphthyl-1'(S)ethyl]-4(R)-hydroxy-3,4,5,6-tetrahydro-2H-pyran-2-one, $I_a$ A mixture of 8.0 g (19.78 mmol) of Compound $III_a$ and 8.31 g (197.8 mmol) of $LiOH.H_2O$ in 600 ml of water is stirred at reflux under a nitrogen atmosphere for 56 hours. The reaction mixture is cooled to 0° and treated, with stirring, with 20 ml of concentrated hydrochloric acid. The mixture is then extracted with three 250 ml portions of ether and the combined extracts are washed successively with three 200 ml portions of water and then 200 ml of saturated brine. After drying over $MgSO_4$, this organic solution is filtered and the solvents evaporated in vacuo to give an oily residue of hydroxy acid $II_a$. This residue is dissolved in 200 ml of toluene and heated at reflux under a nitrogen atmosphere for 2 hours with continuous separation of water to effect relactonization. Evaporation of the toluene and trituration of the residue with hexane gives 5.15 g (81%) of the title compound as white solid which does not require further purification.

An analytical sample is prepared by recrystallization of a portion of this material from butyl chloride to give white clusters: mp 128°-131° (vacuum): NMR(CDCl$_3$) δ 0.87 (d,3,J=7 Hz), 1.16 (d,3,J=7 Hz, $CH_3$), 2.64 (m,2,pyrane $C_3H$'s); 4.27 (brm,1,naphthalene $C_8H$), 4.37 (m,1,pyran $C_4H$); 4.71 (m,1,pyran $C_6H$), 5.56 (m,1,naphthalene $C_5H$), 5.79 (dd,1,J=6,10 Hz, naphthalene $C_3H$), 6.03 (d,1,J=10 Hz,$C_4H$).IR (CHCl$_3$) 3400 (OH), 1725 (C=O), 1240, 1120, 1080 cm$^{-1}$.

Anal. Calcd for $C_{19}H_{28}O_4.0.1C_4H_9Cl$:C,70.67; H, 8.84. Found: C,70.77; H,8.75.

EXAMPLE 2

Alternative preparation of 6(R)-[2-[8'(S)-hydroxy-2'(S), 6'(R)-dimethyl-1',2',4'a,5',6',7',8',8'a(R)-octahydronaphthyl-1'(S)]ethyl]-4(R)-hydroxy-3,4,5,6-tetrahydro-2H-pyran-2-one, $I_d$ A suspension of 188 mg (0.463 mmol) of ($III_d$) in 5 ml (5 mmol) of aqueous 1 N LiOH solution is shaken for 12 hours at 135° in a 30 ml stainless steel pressure vessel. The cooled reaction mixture is acidified with 1 M $H_3PO_4$ and extracted with ethyl acetate. The ethyl acetate solution is dried ($MgSO_4$) and filtered and the solvent is evaporated. The residue is dissolved in 20 ml of toluene which is heated to reflux for 4 hours in a Dean- Stark apparatus to effect relactonization. Evaporation of the toluene gives the compound, $I_d$.

EXAMPLE 3

Preparation of Alcohols $I_b$, $I_c$, and $I_e$

The procedure of either Example I or Example II is followed, using an equivalent amount of esters $III_b$, $III_c$, and $III_e$. The corresponding alcohols $I_b$, $I_c$, and $I_e$ are obtained.

EXAMPLE 4

Preparation of the hydroxy acid $II_a$ and its sodium salt corresponding to the lactone $I_a$ of Example 1

To a solution of $10^{-4}$ mole of the compound $I_a$ in 2 ml of ethanol is added 1 ml of aqueous NaOH ($10^{-4}$ moles; 1 equivalent). After one hour at room temperature, the mixture is taken to dryness in vacuo to yield the sodium salt of Compound $II_a$.

The sodium salt is redissolved in 2 ml of ethanol-water (1:1) and added to 10 ml of 0.1 N hydrochloric acid from which the liberated hydroxy acid is extracted with ethyl acetate. The latter solvent is washed once with water, dried and removed in vacuo with a bath temperature not exceeding 30°. The hydroxy acid slowly reverts to the lactone on standing.

The other hydroxy acids $II_{b-e}$ and their salts are prepared substantially as described in Example 4.

What is claimed is:

1. A compound of the formula

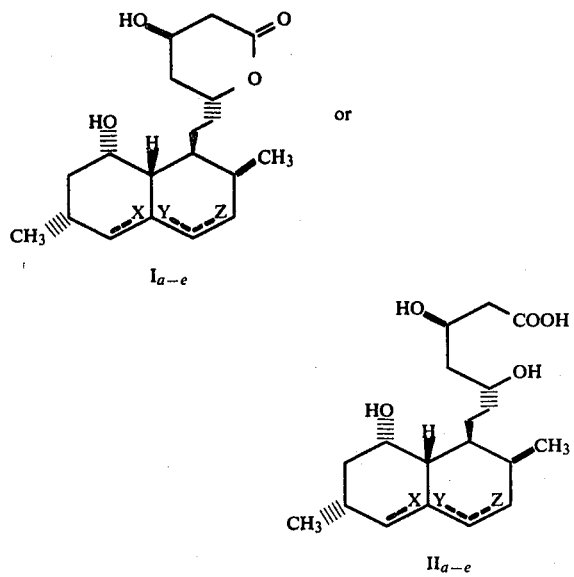

$I_{a-e}$ $II_{a-e}$ in which the dotted lines X, Y and Z represent possible double bonds, said double bonds, when any are present, being either X and Z in combination or one of X, Y or Z alone.

2. A compound of claim 1 in which X and Z represent double bonds.

3. A compound of claim 1 in which X is a double bond.

4. A compound of claim 1 in which Y is a double bond.

5. A compound of claim 1 in which Z is a double bond.

6. A compound of claim 1 in which none of X, Y or Z is a double bond.

* * * * *